(12) United States Patent
Srinivasan et al.

(10) Patent No.: US 9,029,583 B2
(45) Date of Patent: May 12, 2015

(54) PROCESS FOR THE PREPARATION OF FATTY ACID ALKYL ESTERS (BIODIESEL) FROM TRIGLYCERIDE OILS USING ECO-FRIENDLY SOLID BASE CATALYSTS

(75) Inventors: Kannan Srinivasan, Gujarat (IN); Sivashunmugam Sankaranarayanan, Gujarat (IN); Churchil Angel Antonyraj, Gujarat (IN)

(73) Assignee: Council of Scientific & Industrial Research (IN)

( * ) Notice: Subject to any disclaimer, the term of this patent is extended or adjusted under 35 U.S.C. 154(b) by 0 days.

(21) Appl. No.: 13/985,443

(22) PCT Filed: Feb. 10, 2012

(86) PCT No.: PCT/IN2012/000092
§ 371 (c)(1),
(2), (4) Date: Aug. 14, 2013

(87) PCT Pub. No.: WO2012/111023
PCT Pub. Date: Aug. 23, 2012

(65) Prior Publication Data
US 2013/0331587 A1    Dec. 12, 2013

(30) Foreign Application Priority Data
Feb. 14, 2011   (IN) .............................. 371/DEL/2011

(51) Int. Cl.
*C11C 3/00*    (2006.01)
*C07C 67/03*   (2006.01)
*C10L 1/02*    (2006.01)

(52) U.S. Cl.
CPC ........ *C07C 67/03* (2013.01); *C10G 2300/1014* (2013.01); *C10L 1/026* (2013.01); *C11C 3/003* (2013.01); *Y02E 50/13* (2013.01)

(58) Field of Classification Search
USPC ......................................................... 554/167
See application file for complete search history.

(56) References Cited

U.S. PATENT DOCUMENTS

| 7,151,187 B2 | 12/2006 | Delfort et al. |
| 7,420,073 B2 | 9/2008 | Hillion et al. |
| 7,563,915 B2 | 7/2009 | Matson et al. |

FOREIGN PATENT DOCUMENTS

| CN | 1824735 A | 8/2006 |
| CN | 1891786 A | 1/2007 |

(Continued)

OTHER PUBLICATIONS

Gao L et al: "Biodiesel from palm oil via loading KF/Ca-Al hydrotalcite catalyst", Biomass and Bioenergy, Pergamon, Amsterdam, NL, vol. 34, No. 9, Sep. 1, 2010, pp. 1283-1288.*

(Continued)

*Primary Examiner* — Deborah D Carr
(74) *Attorney, Agent, or Firm* — St. Onge Steward Johnston & Reens LLC

(57) ABSTRACT

This invention relates to an improved process for the preparation of green fatty acid methyl esters (FAME; commonly called as biodiesel) from different triglyceride oils using mixed metal oxides derived from layered double hydroxides (referred here as LDHs) as reusable solid heterogeneous base catalysts. This process uses very low alcohohoil molar ratio and catalyst and/or products are easily separable after the reaction through simple physical processes. The properties of thus obtained biodiesel meet the standard biodiesel values and can directly be used as transport fuel.

16 Claims, 6 Drawing Sheets

Triglycerides    Methanol         FAME         Glycerol

(56) References Cited

FOREIGN PATENT DOCUMENTS

| | | |
|---|---|---|
| CN | 101024189 A | 8/2007 |
| CN | 101113349 A | 1/2008 |
| CN | 101185903 A | 5/2008 |
| CN | 101249449 A | 8/2008 |
| CN | 101294094 A | 10/2008 |
| CN | 101314131 A | 12/2008 |
| CN | 101358141 A | 2/2009 |
| CN | 101559359 A | 10/2009 |
| CN | 101608131 A | 12/2009 |
| WO | 2006043281 A1 | 4/2006 |
| WO | 2006050925 A1 | 5/2006 |
| WO | 2010112641 A1 | 10/2010 |

OTHER PUBLICATIONS

Zeng H Y et al: "Activation of Mg-Al hydrotalcite catalysts for transesterification of rape oil", Fuel, IPC Science and Technology Press, Guildford, GB, vol. 87, No. 13-14, Oct. 1, 2008, pp. 3071-3076.*

Gao, et al.; "Biodiesel From Palm Oil Via Loading KF/CA—Al Hydrotalcite Catalyst" Biomass and Bioenergy 34 (2010) 1283-1288.

Zeng, et al.; "Activation of Mg-Al Hydrotalcite Catalysts for Transesterification of Rape Oil"; Fuel 87 (2008) 3071-3076.

Zie, et al.; "Calcined Mg-Al Hydrotalcites as Solid Base Catalysts for Methanolysis of Soybean Oil"; Journal of Molecular Catalysis A: Chemical 246 (2006) 24-32.

Navajas, et al.; "04.Synthesis of Biodiesel From the Methanolysis of Sunflower Oil Using PURAL (R) Mg-Al Hydrotalcites as Catalyst Precursors"; Applied Catalysis B: Evironmental 100 (2011) 299-309.

Guerreiro, et al.; "PVA Embedded Hydrotalcite Membranes as Basic Catalysts for Biodiesel Synthesis by Soybean Oil Methanolysis"; Catalysis Today 156 (2010) 191-197.

Li, et al.; "MgCoAl-LDH Derived Heterogeneous Catalysts for the Ethanol Transesterification of Canola Oil to Biodiesel"; Applied Catalysis B: Environmental 88 (2009) 42-49.

Alvarez, et al.; "Enhanced Use of Renewable Resources: Transesterification of Glycerol Catalyzed by Hydrotalcite-Like Compounds"; Chemical Engineering Journal 161 (2010) 340-345.

Fangrui Ma, et al.; "Biodiesel Production: a Review"; Bioresouce Technology 70 (1999) 1-15.

Gerhard Knothe; "Dependence of Biodiesel Fuel Properties on the Structure of Fatty Acid Alkyl Esters"; Fuel Processing Technology 86 (2005) 1059-1070.

Hideki Fukuda, et al.; "Biodiesel Fuel Production by Transesterification of Oils" Journal of Bioscience and Bioengineering vol. 92, No. 5, 405-416; 2001.

Cantrell, et al.; "Structure-reactivity correlations in MgAl hydrotalcite Catalysts for Biodiesel Synthesis"; Applied Catalysis A: General 287 (2005) 183-190.

Liu, et al.; "Transesterification of Poultry fat with Methanol Using Mg-Al Hydrotalcite Derived Catalysts"; Applied Catalysis A: General 331 (2007) 138-148.

Jonggol Tantirungrotechai, et al.; "Synthesis, Characterization, and Activity in Transesterification of Mesoporous Mg-Al Mixed-Metal Oxides"; Microporous and Mesoporous Materials 128 (2010) 41-47.

Campos-Molina, et al.; "Base Catalysts Derived From Hydrocalumite for the Transesterification of Sunflower Oil"; Energy Fuels 2010, 24, 979-984.

J. Link Shumaker, et al.; "Biodiesel production from soybean oil using calcined Li-Al layered Double Hydroxide Catalysts"; Catalysis Letters, vol. 115, Nos. 1-2; May 2007; 56-61.

Brito, et al.; "Biodiesel Production from Waste Oil Using Mg-Al Layered Double Hydroxide Catalysts"; Energy and Fuels 2009, 23, 2952-2958.

J. Link Shumaker, et al.; "Biodiesel synthesis using calcined layered double hydroxide catalysts" Applied Catalysis B: Environmental 82 (2008) 120-130.

Dae-Won Lee, et al.; "Heterogeneous Base Catalysts for Transesterification in Biodiesel Synthesis"; Catal Surv Asia (2009) 13:63-77.

Tittabut, et al.; "Metal-Loaded MgAl Oxides for Transesterification of Glyceryl Tributyrate and Palm Oil"; Ind. Eng. Chem. Res. 2008; 47, 2176-2181.

Macala, et al.; "Transesterification Catalysts from Iron Doped Hydrotalcite-like Preursors Solid Bases for Biodiesel Production"; Catal Lett (2008) 122:205-209.

Pacharaporn Chuayplod, et al.; "Transesterification of Rice Bran Oil with Methanol Catalyzed by Mg(Al)La Hydrotalcites and Metal MgAl Oxides"; Ind. Eng. Chem. Res. 2009, 48, 4177-4183.

International Preliminary Report on Patentability Application No. PCT/IN2012/000092 Completed: May 24, 2013 7 pages.

International Search Report and Written Opinion of the International Searching Authority Application No. PCT/IN2012/000092 Completed: Jul. 10, 2012; Mailing Date: Jul. 18, 2012 11 pages.

* cited by examiner

PROCESS FOR THE PREPARATION OF FATTY ACID ALKYL ESTERS (BIODIESEL) FROM TRIGLYCERIDE OILS USING ECO-FRIENDLY SOLID BASE CATALYSTS

FIELD OF INVENTION

The invention relates to an improved process for the preparation of fatty acid alkyl-esters (commonly called as biodiesel FAAE) from triglyceride oils and more particularly it relates to the preparation of FAME using reusable solid heterogeneous base catalyst at moderate temperature and ambient atmospheric pressure. Unlike the hitherto known processes, the catalyst and the products are easily separable by simple physical processes. Moreover, the catalyst used is eco-friendly and does not produce any hazardous byproducts.

BACKGROUND OF THE INVENTION

Owing to the depletion of fossil petroleum fuels and their associated environmental polluting effects, research is being focused recently on renewable green alternative plant-derived fuels. Biodiesel is one such alternative for diesel fuels which is non-toxic, eco-friendly and biodegradable renewable fuel. Biodiesel can be prepared from vegetable oils (or) animal fats (or) cooked oils which are largely composed of $C_{14}$-$C_{20}$ fatty acid triglycerides.

A century ago, Rudolf Diesel directly tried peanut oil as transport fuel before the petroleum fuels came in to the market. The paper titled "*Biodiesel production: a review[1]*" by Fangrui Ma et. al. in *Bioresource Technology,* 70 (1999) 1-15, discussed the drawbacks of triglycerides as direct fuels. They reported that some modification processes like blending, microemulsion, thermal cracking (pyrolysis) and transesterification (alcoholysis) are needed to convert oils to transport fuels. Compared to other processes transesterification has many advantages and commonly used for biodiesel production.

Transesterification of triglycerides with short-chain alcohols gives biodiesel. Normally methanol is used because of its high reaction rate, low cost and abundantly available. The paper titled "*Dependence of biodiesel fuel properties on the structure of fatty acid alkyl esters*" by Gerhard Knothe in *Fuel Processing Technology,* 86 (2005) 1059-1070, discussed the variations in the properties of different fatty acid alkyl esters. They suggested that isopropyl esters have better fuel properties than methyl esters; but the cost of iso-propanol is the main disadvantage compared to methanol.

Transesterification reaction is generally carried out by using acid (or) base (or) enzyme catalysts (or) supercritical alcohol conditions. As per the paper titled "*Biodiesel Fuel Production by Transesterification of Oils*" by Hideki Fukuda et. al. in *Journal of Bioscience and Bioengineering, Vol.* 92, *No.* 5 (2001) 405-416, the acid catalyzed transesterification has slow reaction rate. Enzymes catalysis is time consuming and very high in cost than alkali and their activities are relatively low. The use of supercritical methanol requires high temperature of more than 350° C., high pressure of 45 MPa and high methanol amount in catalyst free conditions. Based on this knowledge, base catalyzed transesterification is considered suitable for industrial process.

Currently, in industry homogeneous base catalysts such as NaOH and KOH are used for the biodiesel production. The paper titled "*Heterogeneous Base Catalysts for Transesterification in Biodiesel Synthesis*" by Dae-Won Lee et. al. in *Catalysis Surveys from Asia,* 13 (2009) 63-77, discussed the drawbacks of homogeneous catalysts such as corrosion, catalyst recovery and limitation in continuous process. Further, they have also reported the hurdles/problems such as high reaction temperature (100-250° C.), catalyst amount (3-10 wt %), methanol:oil ratio (10:1-25:1) while using heterogeneous catalysts.

Layered double hydroxides (LDHs; otherwise referred as hydrotalcite-like [HT-like] materials) both in their as-synthesized and heat-treated forms are categorized as heterogeneous base catalysts and can be used for various base catalyzed reactions because of their tunable basicity. There are several reports using heat-treated LDHs as catalysts for biodiesel production.

The paper entitled "*Structure-reactivity correlations in MgAl hydrotalcite catalysts for biodiesel synthesis*" by David G. Cantrell et. al. in *Applied Catalysis A: General,* 287 (2005) 183-190, revealed the biodiesel synthesis from glyceryl tributyrate with methanol. The authors reported both the conversion of glyceryl tributyrate and the yields of methyl butanoate, diglycerides and monoglycerides. They concluded that compared to MgO, oxides derived from MgAl hydrotalcites has higher activity for this reaction. However, the calcination of hydrotalcite (HT) under nitrogen flow and use of high methanol amount are the main drawbacks for this report.

The paper titled "*Calcined Mg—Al hydrotalcites as solid base catalysts for methanolysis of soybean oil*" by Wenlei Xie et. al. in *Journal of Molecular Catalysis A: Chemical,* 246 (2006) 24-32, reported 67% yield of biodiesel with the methanol:oil ratio of 15:1 in 9 h with 7.5 wt % catalyst under refluxing conditions. The drawbacks of this method are high methanol:oil ratio, longer reaction time, relatively lesser yield of biodiesel and fail to address the reusability of the catalyst.

The paper titled "*Biodiesel production from soybean oil using calcined Li—Al layered double hydroxides catalysts*" by J. Link Shumaker et. al. in *Catalysis Letters, Vol.* 115, *No.* 1-2 (2007) 56-61, reports >80% yield of biodiesel using 15:1 methanol:oil ratio and 3 wt % catalyst at reflux temperature in 1 h. Here again the yield is lesser even at high methanol:oil ratio and using more expensive lithium.

The paper entitled "*Transesterification of poultry fat with methanol using Mg—Al hydrotalcite derived catalysts*" by Yijun Liu et. al. in *Applied Catalysis A: General,* 331 (2007) 138-148, discussed the catalysis of both calcined and rehydrated HT-like catalysts for biodiesel synthesis from poultry fats. A maximum conversion of 93% at 120° C. with 30:1 methanol:oil ratio and 10 wt % of catalyst in 8 h was reported. The main drawbacks are process intense variables like heating under inert conditions, high reaction temperature, high catalyst amount and longer time.

The paper titled "*Transesterification Catalysts from Iron Doped Hydrotalcite-like Precursors: Solid Bases for Biodiesel Production*" by Gerald S. Macala et. al. in *Catalysis Letters,* 122 (2008) 205-209, discussed the transesterification of triacetin as well as soybean oil with doped HT-like materials. The 10% Fe-doped hydrotalcite gave 38% of yield of biodiesel after 1 h at 80° C. and 1 wt % catalyst for soybean oil. Their main drawback is the poor activity of the regenerated catalyst.

The paper titled "*Biodiesel synthesis using calcined layered double hydroxide catalysts*" by J. Link Shumaker et. al. in *Applied Catalysis B: Environmental,* 82 (2008) 120-130, reported the biodiesel synthesis from glyceryl tributyrate and soybean oil with methanol over different oxides derived from LDHs. They used high methanol:oil ratio of 15:1 with the oxides Mg—Al, Mg—Fe and Li—Al at reflux temperature and among them Li—Al oxides showed better activity than other oxides. But poor stability of these catalysts is a major drawback for them to be practiced in industrial operations.

The paper titled "*Metal-Loaded MgAl Oxides for Transesterification of Glyceryl Tributyrate and Palm Oil*" by T. Tittabut et. al. in *Industrial & Engineering Chemistry Research*, 47, (2008) 2176-2181, reported the transesterification of glyceryl tributyrate and palm oil with methanol. 96% ester content and 87% yield of biodiesel was reported with the methanol:oil molar ratio of 45:1 at 100° C., 8 wt % catalyst and 9 h reaction time for K loaded MgAl hydrotalcite. The main drawback for this process is the longer time needed for calcination (35 h). The authors reported the recalcination followed by reload of the metal is the way to do the recycle experiment, an energy intensive multi-step operation.

The paper titled "*MgCoAl-LDH derived heterogeneous catalysts for the ethanol transesterification of canola oil to biodiesel*" by Eugena Li et. al. in *Applied Catalysis B: Environmental*, 88 (2009) 42-49, reported ethanol transesterification of canola oil with calcined MgCoAl and MgCoAlLa containing LDHs. A maximum yield of 96-97% at 200° C. using 16:1 of ethanol:oil ratio in 5 h was reported. High temperature and alcohol:oil molar ratio are their drawback.

The paper entitled "*Transesterification of Rice Bran Oil with Methanol Catalyzed by Mg(Al)La Hydrotalcites and Metal/MgAl Oxides*" by Pacharaporn Chuayplod et. al. in *Industrial & Engineering Chemistry Research*, 48 (2009) 4177-4183, reported two-step catalyzed process such as esterification and subsequent transesterification due to the high FFA content in rice bran oil. They reported 97% ester content and 78% yield for the product with rehydrated MgAlLa hydrotalcite at 100° C., 30:1 methanol:oil ratio, 7.5 wt % catalyst and reaction time of 9 h. Their main drawback is the time taken for Mg(Al)La oxide preparation (35 h) and rehydration under nitrogen for 24 h. During reusability tremendous decrease in the yield of biodiesel was noted compared to original catalyst. In order to get the good results, authors suggested the requirement of time-consuming recalcination followed by rehydration process before every cycle.

The paper entitled "*Biodiesel Production from Waste Oil Using Mg—Al Layered Double Hydroxide Catalysts*" by A. Brito et. al. in *Energy Fuels*, 23 (2009) 2952-2958, reported the biodiesel production from sunflower oil and waste oil. They reported the high yield in the temperature range of 120-160° C., methanol:oil ratio of 24:1, 6 wt % catalyst and 6 h reaction time. Their main drawback is intense process variables.

The paper titled "*Synthesis, characterization, and activity in transesterification of mesoporous Mg—Al mixed-metal oxides*" by Jonggol Tantirungrotechai et. al. in *Microporous and Mesoporous Materials*, 128 (2010) 41-47, reported transesterification of soybean using some series of metal impregnated MgAl mixed oxides. They reported >90% yield of biodiesel with methanol:oil ratio of 20:1 at 70° C., 5 wt % catalyst and the reaction time of 8 h. Their main drawbacks are the complicated material synthesis and high methanol amount. They have used high oxygen flow for calcination and carried out overnight drying before the use. Further, the recyclability of the catalysts is not addressed.

The paper entitled "*Base Catalysts Derived from Hydrocalumite for the Transesterification of Sunflower Oil*" by Maria Jose Campos-Molina et. al. in *Energy Fuels*, 24 (2010) 979-984, discussed the catalysis of calcined hydrocalumite for biodiesel production. They reported the 97% yield of biodiesel with 12:1 methanol:oil ratio at 60° C., 1 wt % catalyst and the reaction time of 3 h. The main drawbacks are, resource intense material synthesis (use of ethanol), longer period of activation (13 h) and necessity of preactivation under inert atmosphere, process intense reaction conditions (inert conditions, high methanol:oil ratio) and not reusable for multiple cycles (could do only for two cycles after which the catalyst could not be recovered).

The paper entitled "*Biodiesel from palm oil via loading KF/Ca—Al hydrotalcite catalyst*" by Lijing Gao et. al. in *Biomass and Bioenergy* 34 (2010) 1283-1288 reported the biodiesel production from palm oil using KF/Ca—Al catalyst. The yield of FAME increased with an increase in KF loading and in shorter reaction time. The optimized methanol:oil ratio is 12:1. They recycled the catalyst only for two cycles. The use of expensive KF as an additional reagent and sensitive and time consuming synthetic protocol of the catalyst are the main drawbacks.

The patent (CN 101608131 A) entitled "Method of manufacturing bio-diesel oil without glycerol byproduct" by Zhong Xin et. al. reported that the biodiesel manufacture from vegetable oils and animal fats without glycerol as byproduct. They used alcohol:oil ratio of 1-30:1 at 30-450° C., 0.05-30 MPa for 2-18 h with variety of solid acid/base catalysts and organic base catalysts along with different transesterifying agents like dimethyl carbonate, diethyl carbonate etc. Their main drawback is that the reaction is carried out under high pressures and the usage of costly chemicals.

The patent (WO 2010/112641 A1) entitled "Method for the production of biofuels by heterogeneous catalysis employing a metal zincate as precursor of solid catalysts" by Pedro Jesus Maireles Torres et. al. reported the transesterification of vegetable (or) animal oils or fats for the biodiesel production using calcined zincate of an alk. earth metal (or) of a divalent transition metal. Their main drawbacks are the pre-activation, higher methanol:oil ratio and necessity of inert reaction atmosphere.

The Patent (CN 101559359 A) entitled "Solid base catalyst for preparation of biodiesel by transesterification and its preparation" by Hui Wang et. al. reported the biodiesel preparation from trioleic acid glyceryl ester using KOH treated CaO—ZrO$_2$ at 140-180° C. for 4-6 h. Their main drawbacks are the time consuming preparation of the expensive catalysts and higher reaction temperatures.

The Patent (CN 101314131 A) entitled "Method for preparing modified hydrotalcite solid base catalyst for preparation of biodiesel" by Guomin Xiao et. al. reported the modified hydrotalcite for biodiesel preparation. Their main drawbacks are chemicals demanding and time consuming process to obtain the active catalyst.

The Patent (CN 1824735 A) entitled "Method for preparing biological diesel fuel from *Jatropha curcas* oil using solid catalyst" by Hang Yin et. al. reported the biodiesel preparation from jatropha oil using org. salt of alkali metal and/or alk. earth metal (lithium formate, sodium propionate, etc) and carrier (Al$_2$O$_3$, NaY zeolite, etc) as solid catalyst. Their main drawbacks are the use of expensive chemicals for catalyst preparation and pressure required (0.9 to 1.5 MPa) for the calcination and as well for the reaction.

The patent (U.S. Pat. No. 7,420,073 B2) entitled "Process for the alcoholysis of acid oils of vegetable or animal origin" by Gerard Hillion et. al. reported the biodiesel production using zinc aluminate as catalyst. Their main drawbacks are the high temperature range (180 to 210° C.) and high pressures (4 to 6 MPa).

The Patent (CN 101358141 A) entitled "Method for preparing biodiesel oil from idesia polycarpa maxim. var. vestita diels oil by using solid alkali catalyst" by Hang Song et. al. reported that Mg—Al composite oxide as catalyst for biodiesel preparation. The main drawbacks are the multi-step time consuming process and requirement of many additional chemicals.

The Patent (CN 101294094 A) entitled "Method for producing bio-diesel oil using nanoscale solid heteropoly acid or heteropoly base catalyst" by Heyou Han et. al. reported that biodiesel production using nanoscale solid heteropoly acid (or) heteropoly base catalyst with alcohol:oil ratio of 6-48:1 at 60-90° C. in normal pressure for 1-10 h and 1-6 wt % of catalysts. Heteropoly acid/base catalysts are generally expensive.

The patent (U.S. Pat. No. 7,563,915 B2) entitled "Green biodiesel" by Jack Vincent Matson et. al. reported that solid base catalysts such as simple metal oxides, mixed metal oxides, hydrotalcites and silicates for biodiesel manufacture. They discussed the transesterification of vegetable oil with alcohols (methanol, ethanol) at 60-450° C., 1-500 atmospheres for 5-60 min. Their main drawbacks are the high methanol:oil ratio and high preferred temperature range of 150-260° C.

The Patent (CN 101249449 A) entitled "Preparation and application of new-type solid base catalyst for synthesis of bio-diesel fuel" by Jianguo Yang et. al. reported that the potassium fluoride on different supports like alumina, calcia, dolomite etc. as solid base catalyst for biodiesel synthesis. They used plant oil, animal fat (or) waste oil with low-carbon alcohols (methanol, ethanol, propanol [or] butanol) with different ratios at 50-110° C. for 1-3 h. Such catalysts are generally prone for leaching and fluoride leaching may cause separation/contamination issues.

The Patent (CN 101185903 A) entitled "Manufacture and application of solid base catalyst for synthesizing bio-diesel oil" by Guosheng Zheng et. al. reported that calcium methoxide as catalyst for biodiesel synthesis using animal and vegetable oil with methanol. Calcium methoxide was prepared by firing calcium salts at desired temperature and then cooling with methanol (or) methanolic steam. Their main drawback is the process intense synthesis of catalyst along with likelihood of leaching of calcium.

The Patent (CN 101113349 A) entitled "Production of bio-diesel with convenient post-treatment by esterification of vegetable oil" by Tianbo Weng reported activated magnesium oxide as a catalyst for biodiesel synthesis. He has carried out the transesterification of vegetable oil with alcohols (methanol, ethanol [or] n-butanol) at a ratio of 4-25:1 in the presence of different wt % (0.01-3%) of the catalysts. The main drawbacks are the time consuming procedures to recover the biodiesel and glycerol.

The Patent (WO 2006/050925 A1) entitled "Process for producing esters from vegetable oils or animal fats using heterogeneous catalysts" by Dante Siano et. al. reported that magnesium oxide and magnesium-aluminum mixed oxides derived from hydrotalcite as catalysts for biodiesel production. They used alcohol:oil ratio of 4 to 30:1 at 100 to 250° C. Their main drawback is the high temperature used for this reaction.

The Patent (CN 101024189 A) entitled "Preparation and application of magnetic solid base catalyst for preparation of bio-diesel fuel by transesterification" by Xiaoyong Lu et. al. reported that mixture of different wt % of magnetic material, metal oxide/salt with alkali metal salt as catalyst for biodiesel preparation. They have carried out transesterification reaction for different oils. Their main drawback is the requirement of time consuming preparation of the magnetically separable costlier catalyst.

The Patent (CN 1891786 A) entitled "Production technology of bio-diesel fuel from tallowseed oil" by Yinyu Gao et. al. reported the biodiesel production using alkali, acid, enzyme and solid magnetic catalysts. They have carried out the transesterification of tallowseed oil with lower alcohols at 20-120° C. for 0.5-24 h with 0.1-10 wt % of catalysts. Their main drawback is the use of homogeneous catalysts such as alkali and acids which are making the process as non-ecofriendly. The usage of enzyme is time consuming and expensive.

The Patent (WO 2006/043281 A1) entitled "Improved process for the preparation of fatty acid methyl ester (biodiesel) from triglyceride oil through tranesterification" by Pushpito Kumar Ghosh et. al. reported the biodiesel preparation from *Jatropha curcus* oil using methanolic-KOH solution. The main drawback is the use of corrosive non-reusable alkali-based homogeneous catalyst and associated post-operative clean up.

The patent (U.S. Pat. No. 7,151,187 B2) entitled "Process for transesterification of vegetable oils or animal oils by means of heterogeneous catalysts based on zinc or bismuth, titanium and aluminum" by Bruno Delfort et. al. reported the biodiesel production using heterogeneous catalysts. Their main drawbacks are the usage of high methanol amount and high reaction temperature (200° C.).

OBJECTIVES OF THE INVENTION

The main object of the present invention is to provide an improved process for the preparation of fatty acid alkyl esters from triglyceride oils.

Another object of the present invention is to use reusable solid heterogeneous base catalyst.

Yet another object of the present invention is to use layered double hydroxide derived mixed metal oxide as catalyst.

Still another object of the present invention is to prepare the catalyst precursors using water as solvent and dispensing the need of any other solvent.

Still another object of the present invention is to make use of very low methanol:oil molar ratio.

Still another object of the present invention is the non-requirement of pre-activation of the catalyst before the reaction.

Still another object of the present invention is to carry out the reaction at moderate temperature and ambient atmospheric pressure.

Still another object of the present invention is to adopt simple technique for the separation of catalyst, glycerol and FAME.

Still another object of the present invention is having lower reaction time at moderate temperature and ambient atmosphere to obtain higher yield.

Still another object of the present invention is to obtain FAME with >95% purity.

Still another object of the present invention is to reuse the catalyst for at least four cycles without any loss in efficiency/activity.

Still another object of the present invention is to obtain the byproduct i.e. glycerol with >97% purity.

Still another object of the present invention is to obtain FAME the specification of which matches with the laid down DIN values.

SUMMARY OF THE INVENTION

Accordingly, the present invention provides an improved process for the preparation of fatty acid alkyl esters from triglyceride oils. The present invention discloses the production of FAME by transesterification using eco-friendly solid base catalysts. Production of biodiesel in high yields from different triglyceride oils (edible, non-edible and cooked) at near ambient conditions is achieved, with lesser use of alcohol. Simple method of separation of products is adopted with high recovery of both glycerol and FAME with high purity. The catalyst was reusable. Some of the important properties of the obtained biodiesel matched well with the standard DIN values and can be used directly as fuel.

In an embodiment of the present invention, an improved process for the preparation of fatty acid alkyl esters from different triglyceride oils a using eco-friendly solid base catalyst which comprises of the following steps:
(i) mixing alcohol and triglyceride oil in the molar ratio of alcohol:oil in the range of 1.5:1 to 30:1;
(ii) adding a catalyst to alcohol-oil mixture as obtained in step (i) in the range of 1 to 12 wt % with respect to the triglyceride oil taken;
(iii) heating the reaction mixture as obtained in step (ii) in an oil bath having temperature in the temperature range of 30 to 100° C. for a period in the range of 1 to 24 h;
(iv) filtering the alcohol-oil mixture as obtained in step (iii) to separate the catalyst from the reaction products;
(v) separating the byproduct glycerol from reaction mixture as obtained in step (iv) to obtain FAME;

In another embodiment of the present invention the triglyceride oil used in step (i) is selected from the group consisting of sunflower (*Helianthus annuus*) oil, groundnut (*Arachis hypogaea*) oil, mustard (*Brassica juncea*) oil, palmolein (*Elaeis guineensis*) oil, gingelly (sesame/til; *Sesamum indicum*) oil, ricebran (*Oryza sativa*) oil, cottonseed (*Gossypium arboretum*) oil, corn (*Zea mays*) oil, soyabean (*Glycine max*) oil, castor (*Ricinus communis*) oil, neem (*Azadirachta indica*) oil, atrophy (*Jatropha curcus*) oil, karingatta (*Quassia indica*) oil, marotti (*Hydnocarpus wightiana*) oil, pungai (*Pongamia pinnata*) oil or pinnai (*Calophyllum inophyllum*) oil.

In another embodiment of the present invention acid values of triglyceride oil used in step (i) ranges from 0.5 to 31 mg KOH/g.

In another embodiment of the present invention the cooked and doubly cooked sunflower oil with acid values 1.4 and 2.16 mg KOH/g respectively were used for conversion.

In another embodiment of the present invention the catalyst used in step (ii) is layered double hydroxide with general formula $[M(II)_{1-x}M(III)_x(OH)_2]^{x+}[A_{x/m}^{m-}]^{x-} \cdot nH_2O$ where,
(i) M (II)—divalent metal ions selected from the group $Mg^{2+}$, $Ni^{2+}$, $Co^{2+}$, $Zn^{2+}$, $Ca^{2+}$ and $Li^+$;
(ii) M (III)—trivalent metal ions selected from the group $Al^{3+}$, $Fe^{3+}$ and $Cr^{3+}$;
(iii) A—the interlayer anions selected from the group $CO_3^{2-}$, $Cl^-$ and $NO_3^-$ In another embodiment of the present invention catalyst used in step (ii) was heated at temperature in the range of 100 to 900° C. for a period in the range of 1 to 12 h.

In another embodiment of the present invention alcohol used in step (i) is selected from the group consist of methanol, ethanol, n-propanol, isopropanol or n-butanol In another embodiment of the present invention the reuse of catalyst was carried out for 2 to 4 cycles.

In another embodiment of the present invention yield of fatty acid alkyl esters is in the range of 3-99%.

In another embodiment of the present invention the purity of the fatty acid alkyl esters is >95%

In another embodiment of the present invention, the precursors used for catalytic conversion may be prepared by co-precipitation, urea hydrolysis and hexamine hydrolysis methods using water as solvent.

In still another embodiment of the present invention, glycerol may be recovered as by-product and the amount may be in the range of 90 to 100% (v/v) with purity in the range of 92 to 98%.

In still another embodiment of the present invention, the molecular sieve 3A in granular forms (8-12 mesh) may be used in the range of 3 to 20% (W/N) to reduce the water content in the range of 500-2000 ppm.

DETAILED DESCRIPTION OF THE INVENTION

Figure 1:
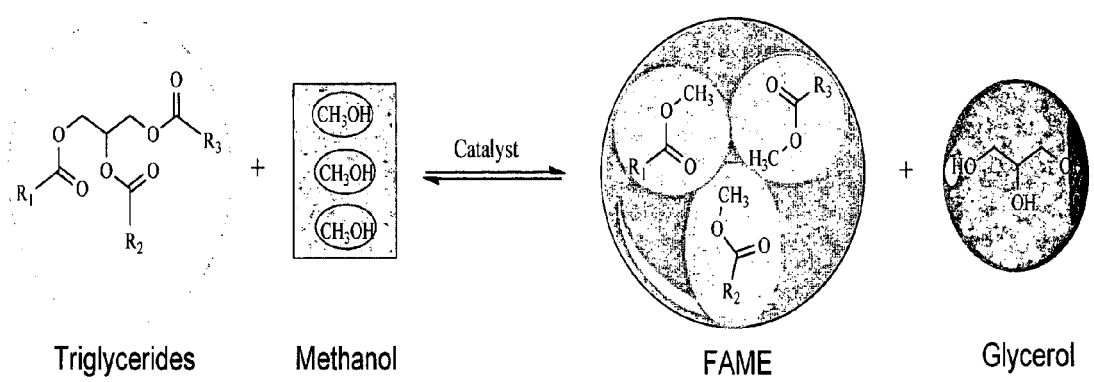
FIG. 1: Reaction scheme for FAME preparation.

The present invention aimed to replace conventional environmentally unfriendly homogeneous trans-esterification process for producing FAME by the eco-friendly heterogeneous process by using heated LDHs as solid base catalysts thereby making the process greener.

Different triglyceride oils (edible, non-edible and cooked) were converted to FAAE most economically by this environmentally benign approach. Catalyst precursors were prepared by using simple precipitation/hydrolysis methods only using water as solvent without many other chemicals. Precursors were heated in static air to obtain active catalyst that did not necessitate pre-activation before the reaction. At very low methanol:oil molar ratio (5.6:1) and at moderate temperature (65° C.) in ambient atmosphere high yields of biodiesel was obtained. Catalyst, glycerol and FAME were separated by the simple and time saving physical separation techniques. FAME yield of >95% was obtained within 5 h of reaction time. Thus prepared catalyst showed an excellent reusability up to four cycles without significant loss in the activity. The obtained glycerol showed >97% purity. The reaction was scaled for one of the oil up to 1 Kg level with similar efficiency (>95% yield). The properties such as density, viscosity, free glycerol, total glycerol, neutralization number and water content of thus obtained FAME met the properties of standard biodiesel (DIN) values.

This present invention relates to an improved process for the preparation of FAME from different triglyceride oils (edible, non-edible and cooked; fatty acid compositions, acid value, saponification value and average molecular weights are given in table 1 and 2) using mixed metal oxides derived from LDHs as reusable solid base heterogeneous catalysts. The catalyst precursors were synthesized by various methods using water as the solvent. The active catalyst was obtained by heating the precursor in the temperature range of 100 to 900° C. for a period in the range of 1 to 12 h in static air in a furnace. Transesterification of different triglyceride oils were carried out with methanol in the methanol:oil molar ratio range of 1.5:1 to 30:1 in the temperature range of 30 to 100° C. using 1 to 12 wt % of catalyst. The catalyst was filtered using known simple filtration technique and glycerol and FAME were separated by conventional known methods. The water content in the FAME was reduced by, passing through the preheated 3A (8-12 mesh) molecular sieves. The yield of FAME was computed by $^1$H NMR. The properties of FAME (such as viscosity, density, total glycerol, free glycerol, neutralization number) and the purity of glycerol were assessed by known methods. The catalyst was recycled by washing with n-hexane and reheated at optimum temperature in static air before reusing.

TABLE 1

| Name of the triglyceride oils | 8:0 | 10:0 | 12:0 | 14:0 | 15:0 | 16:1 | 16:0 | 17:0 | 18:2 | 18:1 a | 18:1 b |
|---|---|---|---|---|---|---|---|---|---|---|---|
| Sunflower oil | — | — | — | 0.2 | 0.04 | 0.3 | 15.3 | 0.1 | 55.4 | 13.1 | — |
| Groundnut oil | — | — | — | 0.1 | — | 0.1 | 19.2 | 0.1 | 48.0 | 10.2 | — |
| Palmolein oil | — | — | 0.3 | 1.9 | 0.1 | 0.2 | 44 | 0.2 | 1.8 | 34.6 | 3.9 |
| Gingelly oil | — | — | — | 0.02 | — | 0.2 | 15.7 | 0.1 | 52.9 | 16.1 | — |
| Mustard oil | — | — | — | 0.03 | — | 0.1 | 2.3 | 0.02 | 19.6 | 15.3 | — |
| Soyabean oil | — | — | — | 0.1 | — | 0.1 | 17.5 | 0.1 | 60.9 | 10.6 | — |
| Cottonseed oil | — | — | — | 1.2 | — | 0.8 | 29.0 | 0.2 | 50.2 | 9.8 | — |
| Corn oil | — | — | 0.1 | 0.1 | — | 0.2 | 23.0 | 0.2 | 57.8 | 9.7 | — |
| Ricebran oil | — | — | — | 0.4 | — | 0.2 | 25.1 | 0.1 | 50.3 | 17.9 | — |
| Jatropha oil | — | — | — | — | — | 1.0 | 18.6 | — | 50.0 | 18.9 | — |
| Pungai oil | 0.4 | 0.4 | 3.8 | 2.3 | — | 0.1 | 23.5 | 0.1 | 2.6 | 48.1 | — |
| Pinnai oil | — | 0.1 | 0.6 | 0.6 | — | 0.2 | 21.6 | 0.1 | 41.7 | 17.5 | — |
| Karingatta oil | — | — | — | 0.3 | — | 0.1 | 19.0 | 0.2 | 52.6 | 12.0 | — |
| Neem oil | — | — | — | — | — | — | 24.8 | — | 17.5 | 32.3 | — |
| Castor oil | — | — | — | — | — | — | 1.6 | — | 6.0 | 3.9 | 0.7 |
| Marotti oil * | — | — | — | — | — | 0.2 | 5.4 | — | 1.1 | 3.5 | — |
| Once cooked (sunflower) oil | — | — | — | — | — | — | 10.2 | — | 71.1 | 11.4 | — |
| Doubly cooked (sunflower) oil | — | — | — | 0.3 | — | 0.9 | 12.0 | — | 57.8 | 17.3 | — |

| Name of the triglyceride oils | 18:1 c | 18:0 | 20:3 | 20:1 | 20:0 | 21:0 | 22:1 | 22:0 | 23:0 | 24:1 | 24:0 |
|---|---|---|---|---|---|---|---|---|---|---|---|
| Sunflower oil | — | 10.9 | 0.3 | 0.4 | 0.8 | — | — | 2.2 | 0.1 | — | 0.8 |
| Groundnut oil | — | 8.7 | — | 1.3 | 2.9 | — | 0.2 | 6.6 | 0.1 | — | 2.6 |
| Palmolein oil | — | 11.5 | — | 0.4 | 0.9 | — | — | 0.2 | 0.04 | — | 0.2 |
| Gingelly oil | — | 12.8 | — | 0.3 | 1.4 | — | — | 0.3 | 0.1 | — | 0.2 |
| Mustard oil | — | 1.5 | — | 9.3 | 1.4 | — | 42.9 | 2.8 | 0.1 | 3.5 | 1.3 |
| Soyabean oil | — | 8.3 | — | 0.4 | 0.8 | 0.07 | — | 0.8 | 0.1 | — | 0.3 |
| Cottonseed oil | — | 5.9 | — | 0.4 | 0.8 | — | 1.1 | 0.5 | 0.1 | 0.1 | 0.2 |
| Corn oil | — | 5.6 | — | 0.8 | 1.3 | — | 0.1 | 0.4 | — | — | 0.6 |
| Ricebran oil | — | 3.1 | — | 0.7 | 1.2 | — | — | 0.4 | — | — | 0.6 |
| Jatropha oil | — | 11.3 | — | — | 0.2 | — | — | — | — | — | — |
| Pungai oil | — | 8.8 | 0.3 | 1.0 | 1.6 | — | 0.7 | 4.9 | — | — | 1.5 |
| Pinnai oil | — | 12.7 | — | 0.5 | 1.4 | — | 0.5 | 1.9 | — | — | 0.7 |
| Karingatta oil | — | 14.6 | — | 0.5 | 0.5 | — | — | 0.1 | — | — | 0.1 |
| Neem oil | — | 23.6 | — | — | 1.8 | — | — | — | — | — | — |
| Castor oil | 86.1 | 1.7 | — | — | — | — | — | — | — | — | — |
| Marotti oil * | — | 1 | — | — | — | — | — | — | — | — | — |
| Once cooked (sunflower) oil | — | 5.0 | — | — | 0.8 | — | — | 1.5 | — | — | — |
| Doubly cooked (sunflower) oil | — | 9.7 | — | 0.3 | 0.5 | — | — | 1.0 | — | — | 0.4 |

(XX:Y = No. of carbon atoms:unsaturated centres)
8:0-Caprylic acid, 10:0-Capric acid, 12:0-Lauric acid, 14:0-Myristic acid, 15:0-pentadecanoic acid, 16:1-Palmitoleic acid, 16:0-Palmitic acid, 17:0-Margaric acid, 18:2-Linoleic acid, 18:1 (a)-Oleic acid, 18:1 (b)-Elaidic acid, 18:1 (c)-Ricinoleic acid, 18:0-Stearic acid, 20:3- Homo-g-linolenic acid, 20:1-(11)-Eicosenoic acid, 20:0-Arachidic acid, 21:0-Heneicosanoic acid, 22:1-Erucic acid, 22:0-Behenic acid, 23:0-Tricosanoic acid, 24:1-(15)-Tetracosenic acid, 24:0-Lignoceric acid,
* 2-Cyclopentene-1-undecanoic acid - 48.7%, 2-Cyclopentene-1-tridecanoic acid - 40.1%.

TABLE 2

| Name of the triglyceride oils | Acid value (mg KOH/g) | Saponification value (mg KOH/g) | Average molecular weight (g/mol) |
|---|---|---|---|
| Sunflower oil | 0.47 | 189.7 | 899 |
| Ground nut oil | 4.49 | 219.7 | 782 |
| Palmolein oil | 1.68 | 238.9 | 710 |
| Gingelly (sesame/til) oil | 3.93 | 219.6 | 780 |
| Mustard oil | 1.12 | 203.6 | 831 |
| Soyabean oil | 0.56 | 218.1 | 774 |
| Cottonseed oil | 0.56 | 210 | 803 |
| Corn oil | 0.56 | 214.9 | 785 |
| Ricebran oil | 2.81 | 216.5 | 788 |
| Jatropha (Jatropha curcus) oil | 30.82 | 259.7 | 736 |
| Pungai (Pongamia pinnata) oil | 10.1 | 235.7 | 714 |
| Pinnai (Calophyllum inophyllum) oil | 20.76 | 234.1 | 789 |
| Karingatta (Quassia indica) oil | 22.44 | 226.1 | 827 |
| Neem (Azadirachta indica) oil | 28.05 | 243.7 | 780 |
| Castor (Ricinus communis) oil | 3.93 | 211.6 | 810 |
| Marotti (Hydnocarpus wightiana) oil | 10.1 | 243.7 | 720 |
| Once cooked (sunflower) oil | 1.40 | 235 | 723 |
| Doubly cooked (sunflower) oil | 2.16 | 267.72 | 634 |

The present invention provide a process for preparing FAAE from different triglyceride oils using eco-friendly solid base catalysts which comprises of the following steps:

(i) Layered double hydroxide with general formula $[M(II)_{1-x}M(III)_x(OH)_2]^{x+}$ $[A_{x-m}{}^{m-}]^{x-}$. $nH_2O$ where, M(II)—divalent metal ions are $Mg^{2+}$, $Ni^{2+}$, $Co^{2+}$, $Zn^{2+}$, Ca$^{2+}$ and Li$^+$; M(III)—trivalent metal ions are Al$^{3+}$, Fe$^{3+}$ and Cr$^{3+}$; A—interlayer anions are CO$_3^{2-}$, Cl$^-$ and NO$_3^-$ used as precursors;
(ii) precursors mentioned in step (i) are prepared by methods like co-precipitation, urea hydrolysis and hexamine hydrolysis using water as the only solvent;
(iii) calcining the precursors as in step (ii) in the temperature of 100 to 900° C. for a period in the range of 1 to 12 h in a static air furnace to obtain the active catalysts;
(iv) taking alcohol, in particular methanol and triglyceride oil in a round bottom flask and varying the molar ratio of methanol:oil in the range of 1.5:1 to 30:1;
(v) adding the catalyst to methanol:oil mixture in the range of 1 to 12 wt %;
(vi) heating the reaction mixture obtained in step (v) in an oil bath in the temp range of 30 to 100° C. for a period in the range of 1 to 24 h at ambient atmosphere;
(vii) filtering the reaction mixture to separate the catalyst from the reaction products;
(viii) separating the byproduct glycerol from FAME;
(ix) recovery of excess methanol by conventional technique for reuse;
(x) treating the FAME with activated 3A (8-12 mesh) type molecular sieve in the range of 3 to 20% (W/V) to reduce the water content.

The present invention provides an improved process of preparation of FAME from different triglyceride oils using heated layered double hydroxide as heterogeneous base catalyst. The unique feature of the invention is that the use of heated layered double hydroxide, as base catalyst at moderate temperature and ambient atmosphere for various triglyceride oils is being reported for the first. Moreover, no hitherto known prior art discloses nor teach how layered double hydroxide can be used as a base catalyst which can be reused up to four cycle without any loss in activity and efficacy. Thus prepared catalyst yields FAME whose properties match with DIN values. Being a heterogeneous catalyst, its separation from the reaction products is simple and devoid of any undesirable byproducts. The inventive steps adopted in the present invention are (i) the precursor to catalyst transformation in static air only once and dispenses the need of pre-activation at higher temperature before the reaction; (ii) the use of heated layered double hydroxide as catalysts obviates the need of the use of homogeneous catalyst; (iii) this base catalyst allows >95% yield at ambient temperature and pressure and does not require higher temperature (or) pressure and/or inert gas ambience for different triglyceride oils; (iv) the process requires very low methanol:oil ratio and needs very less amount of methanol as compared to cited prior art; and (v) the process obviates the need of very long reaction time under inert gas ambience.

EXAMPLES

The following examples are given to illustrate the process of the present invention and should not be construed to limit the scope of the present invention.

Example: 1

5 g (0.0056 mol) of *Helianthus annuus* oil (commonly called as sunflower oil) and 3.2 g (0.0998 mol) of methanol were taken in a 25 ml round bottom (R.B.) flask at 28° C. The methanol:oil molar ratio is 18:1. 150 mg (3 wt % w.r.t. oil) of the MgAl-LDH synthesized by coprecipitation derived catalysts (as-synthesized and heated at 450° C.) was added to the flask. Then the flask was placed in a preheated oil bath and allowed to reflux (65° C.) for 5 h. Methods such as filtration and centrifugation were carried out for the catalyst recovery. Techniques such as saturated NaCl solution washing, hot water washing and phase separation were carried out to separate the glycerol from the FAME. Then the FAME was collected and the excess methanol was distilled out. The methanol free FAME was analyzed by using $^1$H NMR. The yields of FAMEs were 1% for as-synthesized and 4% for heat-treated catalysts.

Example: 2

Figure 2:
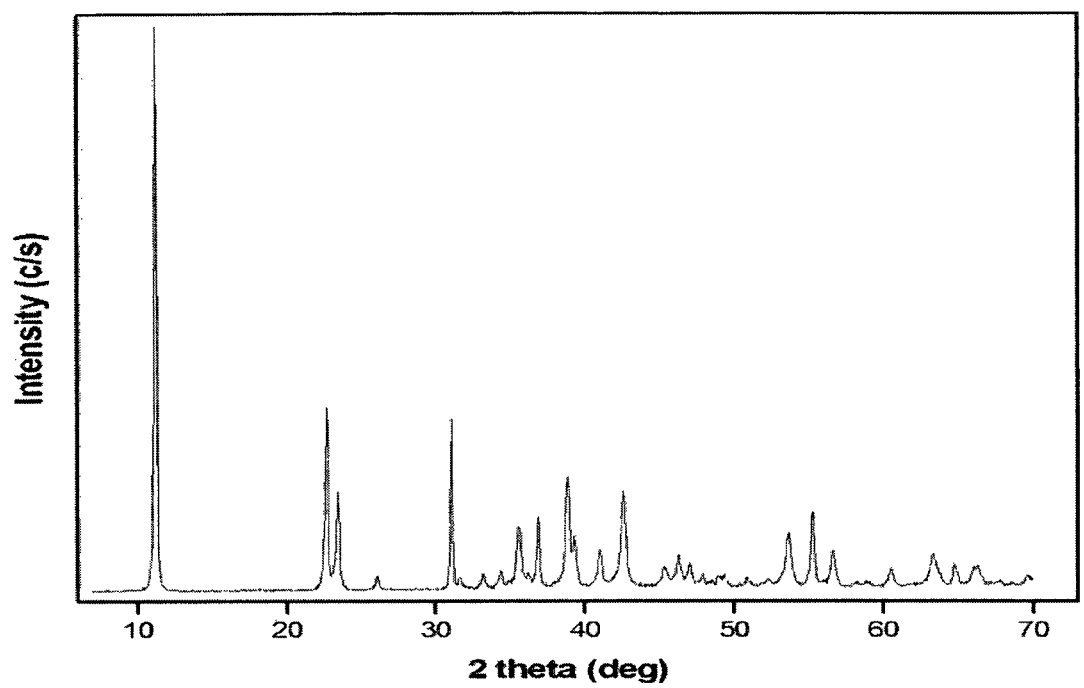
FIG. 2: PXRD of CaAl-LDH

5 g of sunflower oil and 3.2 g of methanol were taken in a 25 ml round bottom (R.B.) flask at 28° C. The methanol: oil molar ratio is 18:1. 150 mg (3 wt % w.r.t. oil) of the LiAl-LDH synthesized by coprecipitation derived catalysts (as-synthesized and heated at 450) was added to the flask. Then the flask was placed in a preheated oil bath and allowed to reflux (65° C.) for 5 h. Catalyst and glycerol was separated from the FAME by using the optimized separating conditions derived from Example 1. The FAME was then collected and the excess methanol was distilled out. The methanol free FAME was analyzed by using $^1$H NMR (shown in FIG. 2). The yields of FAMEs were 1% for as-synthesized and 40% for heat-treated catalysts.

Example: 3

5 g of sunflower oil and 3.2 g of methanol were taken in a 25 ml round bottom (R.B.) flask at 28° C. The methanol:oil molar ratio is 18:1. 150 mg (3 wt % w.r.t. oil) of the CaAl-LDH synthesized by coprecipitation derived catalysts (as-synthesized and heated at 700° C.) was added to the flask. Then the flask was placed in a preheated oil bath and allowed to reflux (65° C.) for 5 h. Further processes were done as mentioned earlier in Example: 2. The yields of FAMEs were 1% for as-synthesized and 85% for heat-treated catalysts.

Example: 4

5 g (0.0056 mol) of sunflower oil and 1 g (0.0312 mol) of methanol were taken in a 25 ml round bottom (R.B.) flask at 28° C. The methanol:oil molar ratio is 5.6:1. 50 mg (1 wt % w.r.t. oil) of the CaAl-LDH catalyst heated at 700° C. was added to the flask. Then the flask was placed in a preheated oil bath and allowed to reflux (65° C.) for 5 h. Further processes were done as mentioned earlier in Example: 2 and the yield of FAME is 60%. Under this reaction conditions, the yields of FAME for different catalysts are given in table 3.

TABLE 3

| Name of the catalyst precursor | Name of the catalyst precursor | Yield of FAME (%) |
| --- | --- | --- |
| CoAl-LDH | Co-precipitation | 0 |
| MgAl-LDH | Co-precipitation | <2 |
| NiAl-LDH | Co-precipitation | 0 |
| ZnAl-LDH | Co-precipitation | 0 |
| CaAl-LDH | Co-precipitation | 60 |
| MgAl-LDH | Urea hydrolysis | 0 |
| MgAl-LDH | Hexamine hydrolysis | 0 |
| CoAl-LDH | Hexamine hydrolysis | 0 |
| NiFe-LDH | Co-precipitation | 0 |
| ZnCr-LDH | Co-precipitation | 0 |

Example: 5

Figure 3:
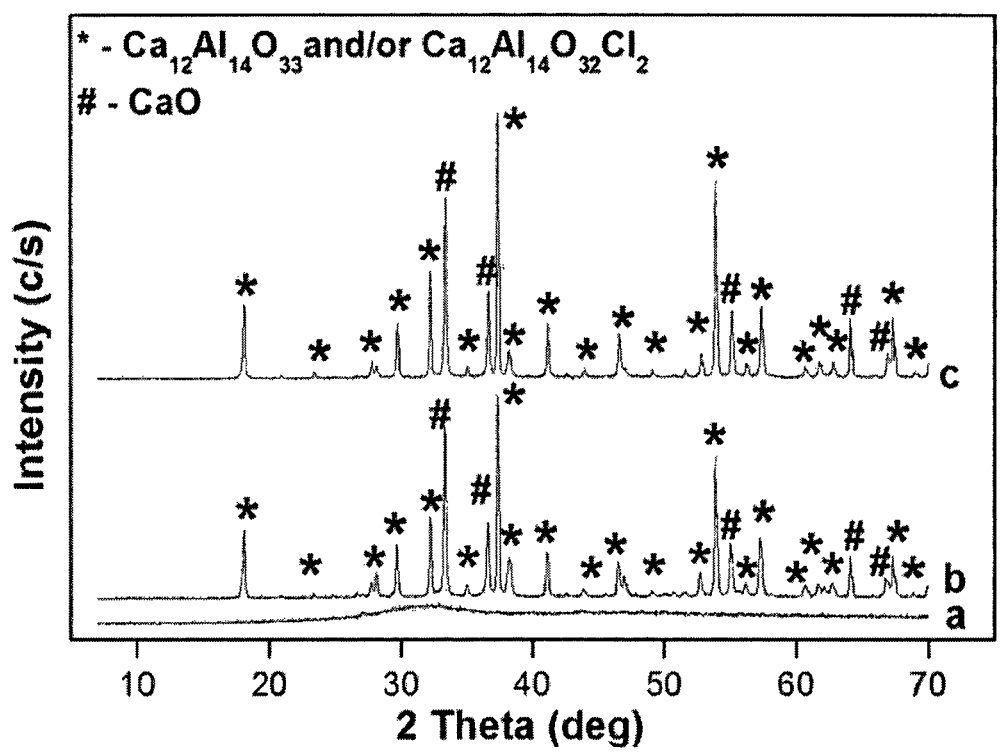
FIG. 3: PXRD of CaAl-LDH heated at different temperature
Figure 4:
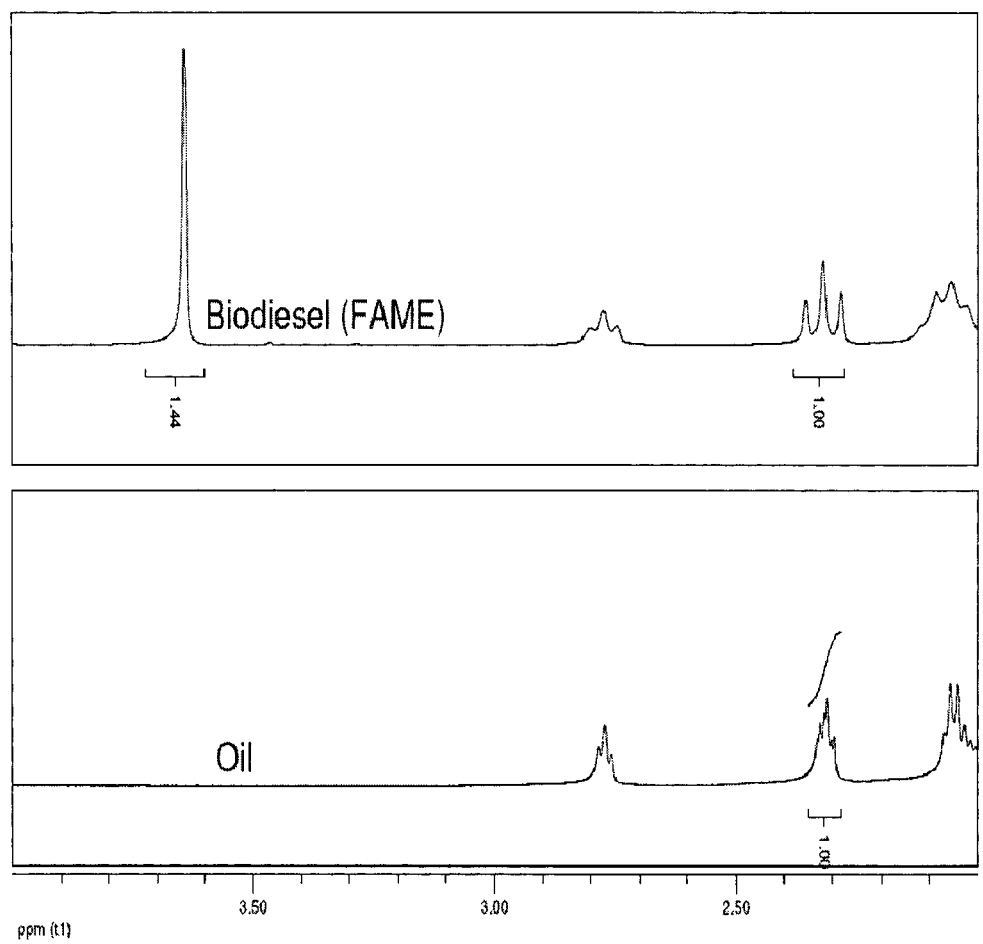
FIG. 4: $^1$H NMR of FAME

5 g of sunflower oil and 1 g of methanol were taken in a 25 ml R.B. flask at 28° C. The methanol:oil molar ratio is 5.6:1. 50 mg (1 wt % w.r.t. oil) of the catalyst was added to the flask. CaAl-LDH (PXRD shown in FIG. 3) was heated at different temperatures in the temperature range of 100-900° C. (PXRD shown in FIG. 4) in static air, and used as catalysts for this reaction. Then the flask was placed in a preheated oil bath and allowed to reflux (65° C.) for 5 h. Further processes were done as mentioned earlier in Example: 2. The results are given in table 4.

TABLE 4

| Calcination temperature (° C.) | Yield of FAME (%) |
|---|---|
| 100 | <1 |
| 200 | 2 |
| 450 | 0 |
| 700 | 60 |
| 900 | 20 |

Example: 6

5 g of sunflower oil and calculated amount (0.27-5.48 g) of methanol were taken in a 25 ml R.B. flask at 28° C. The methanol:oil molar ratio was varied from 1.5:1 to 30:1. 150 mg (3 wt % w.r.t. oil) of the CaAl-LDH catalyst heated at 700° C. (here after referred as CSMCRI-CAT) was added to the flask. Then the flask was placed in a preheated oil bath and allowed to reflux (65° C.) for 5 h. Further processes were done as mentioned earlier in Example: 2. The yield of FAME are given in table 5.

TABLE 5

| Methanol:sunflower oil (molar ratio) | Yield of FAME (%) |
|---|---|
| 1.5:1 | 3 |
| 3:1 | 40 |
| 5.6:1 | 80 |
| 10:1 | 83 |
| 15:1 | 90 |
| 30:1 | 95 |

Example: 7

In a partial modification of the Example: 6, the influence of the multiple addition of methanol under stoichiometric, half excess of the stoichiometric amount and equivalent excess of the stoichiometric amount conditions were checked for this reaction.

5 g of sunflower oil and calculated amount of methanol (0.1-0.75 g) were taken in a 25 ml R.B. flask at 28° C. 150 mg (3 wt % w.r.t. oil) of the CSMCRI-CAT was added to the flask. Then the flask was placed in a preheated oil bath and allowed to reflux (65° C.) for 5 h. The calculated amount of methanol (1 g, methanol:oil molar ratio is 5.6:1) was added in parts that varied from 2 to 10 times. The calculated amount of methanol (0.1-0.75 g) was added to the reaction mixture at different time intervals from 0 to 4.5 h. Further processes were done as mentioned earlier in Example: 2. This process along with the yields of FAME are given in table 6.

TABLE 6

| Addition of methanol amount with time | Yield of FAME (%) |
|---|---|
| One-time addition of 1 g | 80 |
| Initially 0.25 g after 2.5 hours 0.75 g | 74 |
| Initially 0.50 g after 2.5 hours 0.50 g | 58 |
| Initially 0.75 g after 2.5 hours 0.25 g | 47 |
| Initially 0.25 g after 1.5 hours 0.25 g and after 3 hours 0.50 g | 59 |
| Initially 0.25 g every 1.5 hours 0.25 g (1.5 to 4.5 hours) | 31 |
| Initially 0.50 g after 1.5 hour 0.25 g after 3 hours 0.25 g | 69 |
| Initially 0.20 g every 1 hour 0.20 g (1 to 4 hours) | 33 |
| Initially 0.10 g after every half an hour 0.10 g (0.5 to 4.5 hours) | <4 |

5 g of sunflower oil and 1 g of methanol were taken in a 25 ml R.B. flask at 28° C. The initial methanol:oil molar ratio is 5.6:1. 150 mg (3 wt % w.r.t. oil) of the CSMCRI-CAT was added to the flask. Then the flask was placed in a preheated oil bath and allowed to reflux (65° C.) for 5 h. Half excess of the initial stoichiometric methanol (0.5 g) was added to the reaction mixture after 3 h and the reaction was allowed to continue for 5, 10 and 15 h. Further processes were done as mentioned earlier in Example: 2. The yield of FAMEs were 93, 96 and 98% for 5, 10 and 15 h respectively.

5 g of sunflower oil and 1 g of methanol were taken in a 25 ml R.B. flask at 28° C. The initial methanol:oil molar ratio is 5.6:1. 150 mg (3 wt. % w.r.t. oil) of the CSMCRI-CAT was added to the flask. Then the flask was placed in a preheated oil bath and allowed to reflux (65° C.) for 5 h. Equivalent excess of the initial stoichiometric methanol (1 g) was added to the reaction mixture after 3 h and the reaction was allowed to continue for 5 h. Further processes were done as mentioned earlier in Example: 2. The yield of FAME was 99%.

Example: 8

5 g of sunflower oil and 1 g of methanol were taken in a 25 ml R.B. flask at 28° C. The methanol:oil molar ratio is 5.6:1. 150 mg (3 wt % w.r.t. oil) of the CSMCRI-CAT was added to the flask. Then the flask was placed in a preheated oil bath and allowed to reflux (65° C.) for different times from 1 to 24 h. Further processes were done as mentioned earlier in Example: 2. The yields of FAME are given in table 7.

TABLE 7

| Time (h) | Yield of FAME (%) |
|---|---|
| 1 | 30 |
| 3 | 61 |
| 5 | 80 |
| 7.5 | 88 |
| 10 | 87 |
| 15 | 84 |
| 24 | 84 |

Example: 9

Figure 5:
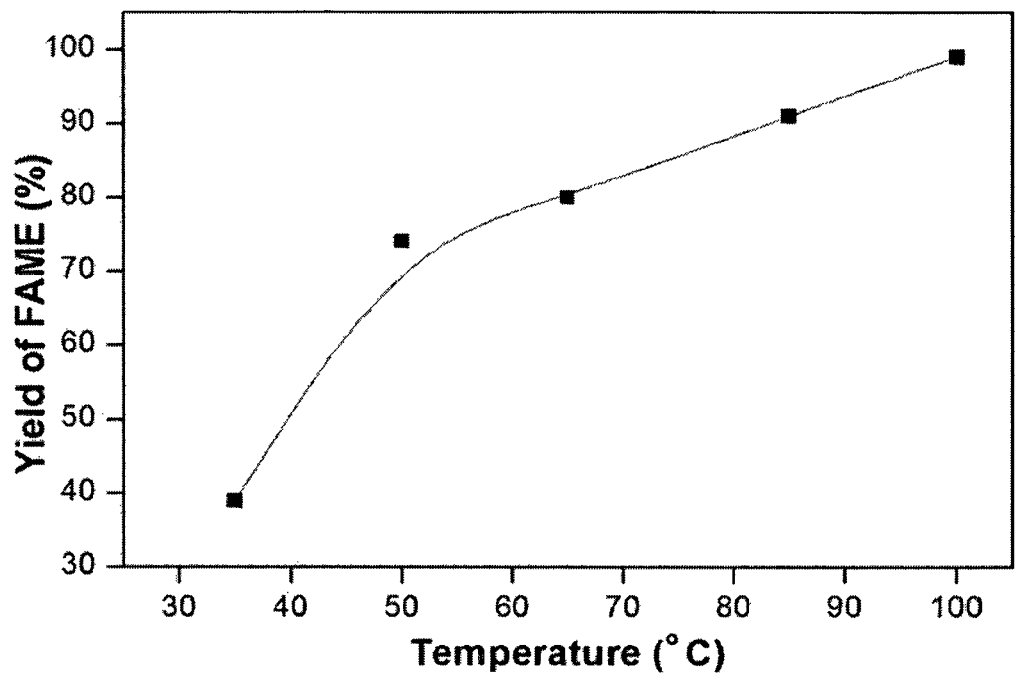
FIG. 5: Yield of FAME at different temperature

5 g of sunflower oil and 1 g of methanol were taken in a 25 ml R.B. flask at 28° C. The methanol:oil molar ratio is 5.6:1. 150 mg (3 wt % w.r.t. oil) of the CSMCRI-CAT was added to the flask. Then the flask was kept at different temperatures from 35 to 100° C. in a preheated oil bath and allowed to reflux (65° C.) for 5 h. Further processes were done as mentioned earlier in Example: 2 and the yields of FAME are shown in FIG. 5.

Example: 10

Figure 6:
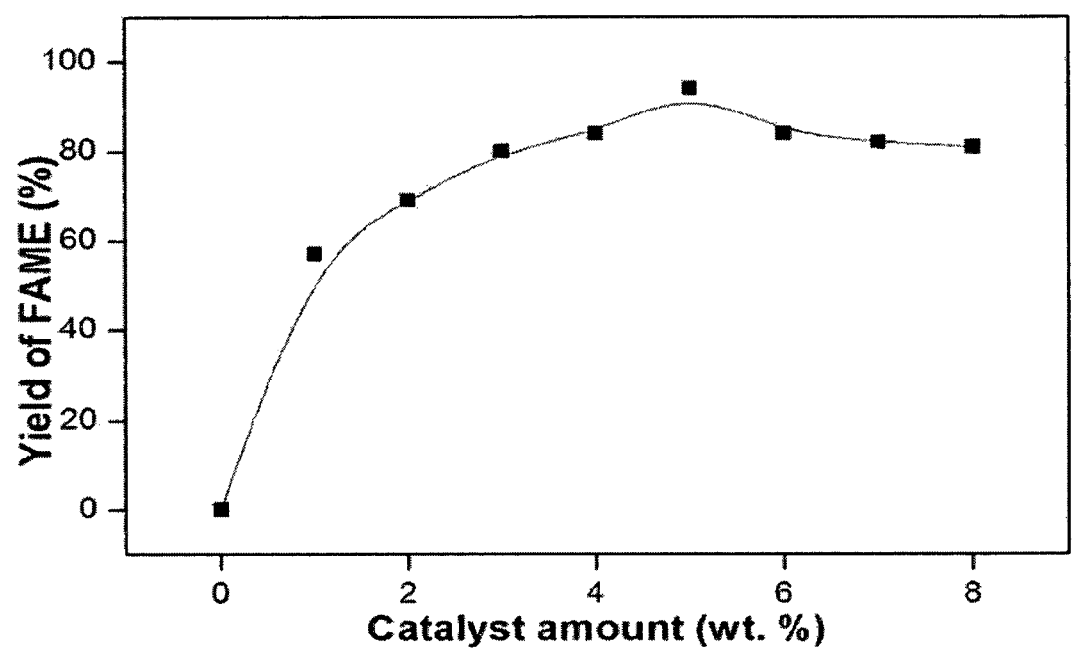
FIG. 6: Yield of FAME with different amount of catalyst

5 g of sunflower oil and 1 g of methanol were taken in a 25 ml R.B. flask at 28° C. The methanol:oil molar ratio is 5.6:1. Different weights in the range 50 to 400 mg (1 to 8 wt % with respect to oil) of the CSMCRI-CAT were added to the flask. Then the flask was placed in a preheated oil bath and allowed to reflux (65° C.) for 5 h. Further processes were done as mentioned earlier in Example: 2. In the absence of the catalyst the yield of FAME was 0%. The yields of FAME are shown in FIG. 6.

In order to check the heterogeneity of the catalyst, 250 mg of CSMCRI-CAT was taken along with 1 g of methanol in a 25 ml R.B. flask at 28° C. Then the flask was placed in a preheated oil bath and allowed to reflux (65° C.) for 1 h. The catalyst was recovered by centrifugation and the methanolic centrifugate was mixed with sunflower oil and reaction was carried out 65° C. for 5 h. The yield of FAME was 0% that confirms the reaction is heterogeneously catalyzed in nature.

Example: 11

5 g of sunflower oil and 1 g of methanol were taken in a 25 ml R.B. flask 28° C. The methanol:oil molar ratio is 5.6:1. 250 mg (5 wt % w.r.t. oil) of the CSMCRI-CAT was added to the flask. Then the flask was placed in a preheated oil bath and allowed to reflux for 5 h. Further processes were done as mentioned earlier in Example: 2. The recovered catalyst was washed well with n-hexane and reheated at 700° C. and reused. The yields of FAME were 96, 87, 85 and 77% for subsequent cycles.

Example: 12

Scale up studies with respect to Example 11 at 2, 5, 20 and 200 times was done. Calculated amount of sunflower oil (10, 25, 100 and 1000 g) and calculated amount of methanol (2, 5, 20 and 200 g respectively) were taken in a R.B. flask at 28° C. The methanol:oil molar ratio is 5.6:1. Calculated amount (0.5, 1.25, 5 and 50 g respectively) of CSMCRI-CAT was added to the flask. Then the flask was placed in a preheated oil bath and allowed to reflux (65° C.) for 5 h except for 1000 g reaction that was kept for 6 h. Further processes were done as mentioned earlier in Example: 2. The yields of FAME are given in table 8.

TABLE 8

| Oil amount (g) | Yield of FAME (%) |
|---|---|
| 10 | 95 |
| 25 | 96 |
| 100 | 95 |
| 1000 | 97 |

In 5 times scaled up reaction, the density of the FAME was 0.880 kg/m$^3$, the viscosity at 40° C. was 5.1 cp, the free glycerol was 0.103 g/100 g, and the total glycerol was 0.388 g/100 g. The obtained FAME amount was ~20 g and the obtained glycerol amount was ~2.5 g.

In 20 times scaled up reaction, the density of the FAME was 870 kg/m$^3$, the viscosity at 25° C. was 7.3 cp, the neutralization number was 0.14 mg KOH/g, the free glycerol was 0.208 g/100 g, the total glycerol was 0.461 g/100 g. The obtained FAME amount was ~90 g and the obtained glycerol amount was ~9.5 g.

In 200 times scaled up reaction, the density of the FAME was 857 kg/m$^3$, the viscosity at 25° C. was 7.4 cp, the neutralization number was 0.53 mg KOH/g, the free glycerol was 0.166 g/100 g, the total glycerol was 0.516 g/100 g and the water content was 2000 mg/kg. In order to reduce the water content, calculated amount of FAME was passed through the calculated amount of the activated 3A (8-12 mesh) molecular sieves. The water content was reduced to 780 mg/kg. The obtained FAME amount was ~800 g (excluding handling loss) and the obtained glycerol amount was ~85 g. The purity of FAME and glycerol are >95 and >97% respectively.

Example: 13

5 g of sunflower oil and 1 g of methanol were taken in a 25 ml R.B. flask at 28° C. The methanol:oil molar ratio is 5.6:1. 250 mg of CSMCRI-CAT was added to the flask. Then the flask was placed in a preheated oil bath and allowed to reflux (65° C.) for 5 h in air and nitrogen atmosphere. Further processes were done as mentioned earlier in Example: 2. The yields of FAME were 92 and 91% respectively. Use of LR grade methanol that had considerable water content (0.05%) also gave similar yield of biodiesel. Even deliberate addition of water (up to 2%) showed only a marginal decrease in the yield of FAME (from 95% to 88% with 1% water and 80% with 2% water).

Example: 14

5 g of sunflower oil and 1 g of methanol were taken in a 25 ml R.B. flask at 28° C. The methanol:oil molar ratio is 5.6:1. CaO/101.5 mg (or) Al$_2$O$_3$/42.5 mg (or) physical mixture of CaO/101.5 & Al$_2$O$_3$/42.5 mg (equal to the amount present in LDH derived oxides) which are derived from the corresponding hydroxides was added to the flask. Then the flask was placed in a preheated oil bath and allowed to reflux (65° C.) for 5 h. Further processes were done as mentioned earlier in Example: 2. The yields of FAME were 81, 0 and 62% for CaO, Al$_2$O$_3$ and physical mixture mentioned above, respectively.

Example: 15

In one another Example, different alcohols such as ethanol, n-propanol, isopropanol and n-butanol were used instead of methanol. 5.6:1 alcohol:oil molar ratio was taken in the 25 ml R.B. flask at 28° C. 250 mg of CSMCRI-CAT was added to the flask. The flask was then placed in a preheated oil bath near to their boiling point and allowed to reflux (ethanol=80° C., n-propanol=97° C., isopropanol=84° C., n-butanol=118° C.) for 5 h. The yield of FAAE (biodiesel) was calculated based on the isolated glycerol weight. The results are shown in table 9.

TABLE 9

| Name of the alcohol | Yield of FAAE (biodiesel) (%) |
|---|---|
| Ethanol | 88 |
| n-propanol | 86 |
| Isopropanol | 86 |
| n-butanol | 85 |

Example: 16

5 g (0.0064 mol) of *Arachis hypogaea* oil (commonly called as groundnut oil) and 1 g (0.0312 mol) of methanol were taken in a 25 ml R.B. flask at 28° C. The methanol:oil molar ratio is 4.9:1. 250 mg (5 wt % w.r.t. oil) of the CSM- CRI-CAT was added to the flask. Then the flask was placed in a preheated oil bath and allowed to reflux (65° C.) for 5 h. Further processes were done as mentioned earlier in Example: 2. The yield of FAME was 95%.

Example: 17

5 g (0.006 mol) of *Brassica juncea* oil (commonly called as mustard oil) and 1 g (0.0312 mol) of methanol were taken in a 25 ml R.B. flask at 28° C. The methanol:oil molar ratio is 5.2:1. 250 mg (5 wt % w.r.t. oil) of the CSMCRI-CAT was added to the flask. Then the flask was placed in a preheated oil bath and allowed to reflux (65° C.) for 5 h. Further processes were done as mentioned earlier in Example: 2. The yield of FAME was 93%.

Example: 18

5 g (0.007 mol) of *Elaeis guineensis* oil (commonly called as palmolein oil) and 1 g (0.0312 mol) of methanol were taken in a 25 ml R.B. flask at 28° C. The methanol:oil molar ratio is 4.5:1. 250 mg (5 wt % w.r.t. oil) of the CSMCRI-CAT was added to the flask. Then the flask was placed in a preheated oil bath and allowed to reflux (65° C.) for 5 h. Further processes were done as mentioned earlier in Example: 2. The yield of FAME was 97%.

Example: 19

5 g (0.0064 mol) of *Sesamum indicum* oil (commonly called as gingelly/sesame/til oil) and 1 g (0.0312 mol) of methanol were taken in a 25 ml R.B. flask at 28° C. The methanol:oil molar ratio is 4.9:1. 250 mg (5 wt % w.r.t. oil) of the CSMCRI-CAT was added to the flask. Then the flask was placed in a preheated oil bath and allowed to reflux (65° C.) for 5 h. Further processes were done as mentioned earlier in Example: 2. The yield of FAME was 97%.

Example: 20

5 g (0.0063 mol) of *Oryza sativa* oil (commonly called as ricebran oil) and 1 g (0.0312 mol) of methanol were taken in a 25 ml R.B. flask at 28° C. The methanol:oil molar ratio is 4.9:1. 500 mg (10 wt % w.r.t. oil) of the CSMCRI-CAT was added to the flask. Then the flask was placed in a preheated oil bath and allowed to reflux (65° C.) for 5 h. Further processes were done as mentioned earlier in Example: 2. The yield of FAME was 91%.

Example: 21

5 g (0.0062 mol) of *Gossypium arboretum* oil (commonly called as cottonseed oil) and 1 g (0.0312 mol) of methanol were taken in a 25 ml R.B. flask at 28° C. The methanol:oil molar ratio is 5:1. 250 mg (5 wt % w.r.t. oil) of the CSMCRI-CAT was added to the flask. Then the flask was placed in a preheated oil bath and allowed to reflux (65° C.) for 5 h. Further processes were done as mentioned earlier in Example: 2. The yield of FAME was 97%.

Example: 22

5 g (0.0064 mol) of *Zea mays* oil (commonly called as corn oil) and 1 g (0.0312 mol) of methanol were taken in a 25 ml R.B. flask at 28° C. The methanol:oil molar ratio is 4.9:1. 250 mg (5 wt % w.r.t. oil) of the CSMCRI-CAT was added to the flask. Then the flask was placed in a preheated oil bath and allowed to reflux (65° C.) for 5 h. Further processes were done as mentioned earlier in Example: 2. The yield of FAME was 97%.

Example: 23

5 g (0.0064) of *Glycine max* oil (commonly called as soyabean oil) and 1 g (0.0312 mol) of methanol were taken in a 25 ml R.B. flask at 28° C. The methanol: oil molar ratio is 4.9:1. 250 mg (5 wt % w.r.t. oil) of the CSMCRI-CAT was added to the flask. Then the flask was placed in a preheated oil bath and allowed to reflux (65° C.) for 5 h. Further processes were done as mentioned earlier in Example: 2. The yield of FAME was 94%.

Example: 24

5 g (0.0062 mol) of *Ricinus communis* oil (commonly called as castor oil) and 2 g (0.0624 mol) of methanol were taken in a 25 ml R.B. flask at 28° C. The methanol:oil molar ratio is 10.1:1. 250 mg (5 wt % w.r.t. oil) of the CSMCRI-CAT was added to the flask. Then the flask was placed in a preheated oil bath and allowed to reflux (65° C.) for 5 h. Further processes were done as mentioned earlier in Example: 2. The yield of FAME was calculated based $^1$H NMR and also the isolated glycerol weight. The yield of FAME was 70%.

Example: 25

5 g (0.0064 mol) of *Azadirachta indica* oil (commonly called as neem oil) and 2 g (0.0624 mol) of methanol were taken in a 25 ml R.B. flask at 28° C. The methanol:oil molar ratio is 9.7:1. 250 mg (5 wt % w.r.t. oil) of the CSMCRI-CAT was added to the flask. Then the flask was placed in a preheated oil bath and allowed to reflux (65° C.) for 5 h. Further processes were done as mentioned earlier in Example: 2. The yield of FAME was 99%.

Example: 26

5 g (0.0068 mol) of *Jatropha curcus* oil (commonly called as jatropha oil) and 1 g (0.0312 mol) of methanol were taken in a 25 ml R.B. flask at 28° C. The methanol:oil molar ratio is 4.6:1. 600 mg (12 wt % w.r.t. oil) of CSMCRI-CAT was added to the flask. Then the flask was placed in a preheated oil bath and allowed to reflux (65° C.) for 5 h. Further processes were done as mentioned earlier in Example: 2. The yield of FAME was 95%.

Example: 27

5 g (0.0060 mol) of *Quassia indica* oil (commonly called as karingatta oil) and 1 g (0.0312 mol) of methanol were taken in a 25 ml R.B. flask at 28° C. The methanol:oil molar ratio is 5.2:1. 300 mg (6 wt % w.r.t. oil) of the CSMCRI-CAT was added to the flask. Then the flask was placed in a preheated oil bath and allowed to reflux (65° C.) for 5 h. Further processes were done as mentioned earlier in Example: 2. The yield of FAME was 99%.

Example: 28

5 g (0.0069 mol) of *Hydnocarpus wightiana* oil (commonly called as marotti oil) and 1 g (0.0312 mol) of methanol were taken in a 25 ml R.B. flask at 28° C. The methanol:oil molar ratio is 4.5:1. 250 mg (5 wt % w.r.t. oil) of the CSM- CRI-CAT was added to the flask. Then the flask was placed in a preheated oil bath and allowed to reflux (100° C.) for 5 h. Further processes were done as mentioned earlier in Example: 2. The yield of FAME was 62%.

Example: 29

5 g (0.0070 mol) of *Pongamia pinnata* oil (commonly called as pungai/honge/karanja oil) and 1 g (0.0312 mol) of methanol were taken in a 25 ml R.B. flask at 28° C. The methanol:oil molar ratio is 4.5:1. 250 mg (5 wt % w.r.t. oil) of the CSMCRI-CAT was added to the flask. Then the flask was placed in a preheated oil bath and allowed to reflux (65° C.) for 5 h. Further processes were done as mentioned earlier in Example: 2. The yield of FAME was 96%.

Example: 30

5 g (0.0063 mol) of *Calophyllum inophyllum* oil (commonly called as pinnai oil) and 2 g (0.0624 mol) of methanol were taken in a 25 ml R.B. flask at 28° C. 2 The methanol:oil molar ratio is 9.9:1. 50 mg (5 wt % w.r.t. oil) of the CSMCRI-CAT was added to the flask. Then the flask was placed in a preheated oil bath and allowed to reflux (65° C.) for 5 h. Further processes were done as mentioned earlier in Example: 2. The yield of FAME was 99%.

Example: 31

5 g of cooked sunflower oil (once; 0.0069 mol/doubly; 0.0079 mol) and 1 g (0.0312 mol) of methanol were taken in a 25 ml R.B. flask at 28° C. The methanol:oil molar ratio is 4.5:1 & 4:1 respectively. 350 mg (7 wt % w.r.t. oil) of the CSMCRI-CAT was added to the flask. Then the flask was placed in a preheated oil bath and allowed to reflux (65° C.) for 5 h. Further processes were done as mentioned earlier in Example: 2. The yield of FAME was 95% for both cases.

Advantages of the Invention

- Improved and greener process for FAAE preparation from different triglyceride oils (edible, non-edible and cooked) (acid values ranges from 0.5 to 31 mg KOH/g) using heated LDHs as inexpensive solid base heterogeneous catalysts without using any additional reagents or promoters.
- Use of water alone as the reaction medium (or solvent) for the synthesis of LDH precursors.
- Low methanol:oil molar ratio used in our process compared to other heterogeneous systems known to the prior art.
- Maximum yield of >95% at low methanol:oil ratio and at moderate temperature in ambient atmosphere within 5 h.
- Obtaining high yield of FAME using the catalyst without any pre-activation.
- Separation of the catalyst, glycerol from FAME by simple physical methods that makes the process time-efficient.
- The catalyst is being recyclable is one of the many advantages in our process.
- High catalytic activity of LDH derived mixed oxides compared to the physical mixture of individual oxides.
- High yield & purity of the obtained biodiesel.
- High recovery of glycerol (90 to 100% (v/v)) with high purity (92 to 98%).
- Scaling up to 1 Kg level (for sunflower oil) with similar efficiency as that of lab scale.
- The properties of our FAME satisfy the standard (DIN) biodiesel values and can directly be used as transport fuel.

We claim:

1. A process for the preparation of fatty acid alkyl-esters (FAAE) from triglyceride oils selected from the group consisting of sunflower (*Helianthus annuus*) oil, groundnut (*Arachis hypogaea*) oil, mustard (*Brassica juncea*) oil, palmolein (*Elaeis guineensis*) oil, gingelly (sesame/til; *Sesamum indicum*) oil, ricebran (*Oryza sativa*) oil, cottonseed (*Gossypium arboretum*) oil, corn (*Zea mays*) oil, soyabean (*Glycine max*) oil, castor (*Ricinus communis*) oil, neem (*Azadirachta indica*) oil, Jatrophy (*Jatropha curcus*) oil, karingatta (*Quassia indica*) oil, marotti (*Hydnocarpus wightiana*) oil, pungai (*Pongamia pinnata*) oil, and pinnai (*Calophyllum inophyllum*) oil using a solid base catalysts, the process comprising the steps of:
   (i) mixing alcohol and triglyceride oil in a molar ratio of alcohol: oil in the range of 1.5:1 to 30:1;
   (ii) adding a catalyst to the alcohol-oil mixture as obtained in step (i) in the range of 1 to 12 wt % with respect to the triglyceride oil, wherein the catalyst is a layered double hydroxide with the gereral formula $[M(II)_{1-x}M(III)_x(OH)_2]^{x+}[A_{x/m}{}^{m-}]^{x-}\cdot nH_2O$, wherein
   M (II) is $Ca^{2+}$;
   M (III) is $Al^{3+}$; and
   A is interlayer anions selected from the group $CO_3^{2-}$, $Cl^-$ and $NO_3^-$; and wherein the catalyst is calcined at a temperature of 700° C. for 1 to 12 hours prior to being used in step (ii);
   (iii) heating the alcohol-oil mixture as obtained in step (ii) at a temperature in the range of 30 to 100° C. for a period in the range of 1 to 24 hours to form a reaction mixture;
   (iv) filtering the reaction mixture as obtained in step (iii) to separate the catalyst from a filtrate, the filtrate containing glycerol and fatty add alkyl esters; and
   (v) separating glycerol from the filtrate as obtained in step (iv) to obtain the fatty acid alkyl esters.

2. The process as claimed in claim 1, wherein an acid value of triglyceride oil used in step (i) ranges from 0.5 to 31 mg KOH/g.

3. The process as claimed in claim 1, wherein the triglyceride oil used is sunflower oil.

4. The process as claimed in claim 3, wherein the sunflower oil is cooked or doubly cooked sunflower oil having an acid value 1.4 and 2.16 mg KOH/g respectively.

5. The process as claimed in claim 1, wherein alcohol used in step (i) is selected from the group consisting of methanol, ethanol, n-propanol, isopropanol, and n-butanol.

6. The process as claimed in claim 1, wherein the catalyst is reused for 2 to 4 cycles.

7. The process as claimed in claim 1, wherein yield of the fatty acid alkyl-esters is in the range of 3-99%.

8. The process as claimed in claim 1, wherein purity of the fatty acid alkyl-esters is >95%.

9. The process as claimed in claim 1, wherein the molar ratio of alcohol: oil is 5.6:1.

10. The process as claimed in claim 9, wherein the catalyst is 5 wt % with respect to the triglyceride oil taken.

11. The process as claimed in claim 6, wherein the reuse of the catalyst comprises the step of reheating the catalyst separated from step (iv) at a temperature of 700° C.

12. The process as claimed in claim 11, wherein yield of the fatty acid alkyl-esters after 4 cycles of use is no less than 77%.

13. A process for the preparation of fatty acid alkyl-esters (FAAE) comprising the steps of:
   (i) mixing methanol and sunflower oil in a molar ratio of methanol : sunflower oil of 5.6:1;
   (ii) adding a catalyst to the methanol and sunflower oil mixture as obtained in step (i) wherein the catalyst is 5 wt % with respect to the sunflower oil, and wherein the catalyst is a layered double hydroxide with the general formula $[M(II)_{1-x}M(III)_x(OH)_2]^{x+}[A_{x/m}{}^{m-}]^{x-}\cdot nH_2O$, wherein M (II) is $Ca^{2+}$;

M (III) is $Al^{3+}$; and

A is interlayer anions selected from the group $CO_3{}^{2-}$, $Cl^-$ and $NO_3{}^-$; and wherein the catalyst is calcined at a temperature of 700° C for 1 to 12 hours prior to being used in step (ii);

(iii) heating the methanol and sunflower oil mixture as obtained in step (ii) to a reflux temperature for a period of about 5 hours to form a reaction mixture;

(iv) filtering the reaction mixture as obtained in step (iii) to separate the catalyst from a filtrate, the filtrate containing glycerol and fatty acid alkyl esters; and (v) separating glycerol from the filtrate as obtained in step (iv) to obtain the fatty acid alkyl esters.

14. The process as claimed in claim 13, wherein the catalyst separated from step (iv) reheated at a temperature of 700° C. and reused in the process cycle of steps (i) to (v), wherein yield of the fatty acid alkyl-esters after 4 cycles of use is no less than 77%.

15. A process for the preparation of fatty acid alkyl-esters (FAAE) from triglyceride oils selected from the group consisting of consisting of sunflower (*Helianthus annuus*) oil, groundnut (*Arachis hypogaea*) oil, mustard (*Brassica juncea*) oil, palmolein (*Elaeis guineensis*) oil, gingelly (sesame/til; *Sesamum indicum*) oil, ricebran (*Oryza sativa*) oil, cottonseed (*Gossypium arboretum*) oil, corn (*Zea mays*) oil, soyabean (*Glycine max*) oil, castor (*Ricinus communis*) oil, neem (*Azadirachta indica*) oil, Jatrophy (*Jatropha curcus*) oil, karingatta (*Quassia indica*) oil, marotti (*Hydnocarpus wightiana*) oil, pungai (*Pongamia pinnata*) oil, and pinnai (*Calophyllum inophyllum*) oil using a solid base catalyst, the process comprising the steps of:

(i) mixing alcohol and triglyceride oil in a molar ratio of alcohol: oil in the range of 1.5:1 to 30:1;

(ii) adding a catalyst to the alcohol-oil mixture as obtained in step (i) in the range of 1 to 12 wt % with respect to the triglyceride oil, wherein the catalyst is a layered double hydroxide with the gereral formula $[M(II)_{1-x}M(III)_x(OH)_2]^{x+}[A_{x/m}{}^{m-}]^{x-}\cdot nH_2O$, wherein M (II) is $Li^+$;

M (III) is $Al^{3+}$; and

A is interlayer anions selected from the group $CO_3{}^{2-}$, $Cl^-$ and $NO_3{}^-$; and wherein the catalyst is calcined at a temperature of 450° C. for 1 to 12 hours prior to being used in step (ii);

(iii) heating the alcohol-oil mixture as obtained in step (ii) at a temperature in the range of 30 to 100° C. for a period of 1 to 24 hours to form a reaction mixture;

(iv) filtering the reaction mixture as obtained in step (iii) to separate the catalyst from a filtrate, the filtrate containing glycerol and fatty acid alkyl esters; and (v) separating glycerol from the filtrate as obtained in step (iv) to obtain the fatty acid alkyl esters.

16. The process as claimed in claim 15, wherein the triglyceride oil used is sunflower oil.

* * * * *